(12) United States Patent
Paige

(10) Patent No.: US 6,394,879 B1
(45) Date of Patent: May 28, 2002

(54) POSTPARTUM BRASSIERE

(76) Inventor: Christine M. Paige, 22190 Wingate Ct., Farmington Hills, MI (US) 48335

( * ) Notice: Subject to any disclaimer, the term of this patent is extended or adjusted under 35 U.S.C. 154(b) by 0 days.

(21) Appl. No.: 09/779,999

(22) Filed: Feb. 9, 2001

(51) Int. Cl.[7] .............................................. A41C 3/00
(52) U.S. Cl. ........................... 450/38; 450/1; 607/108; 607/104
(58) Field of Search ................................ 450/38, 57, 58, 450/36, 37, 1; 2/102, 104–106, 267, 268; 607/108, 110, 104, 96; 623/7.8

(56) References Cited

U.S. PATENT DOCUMENTS

| | | | |
|---|---|---|---|
| 1,391,936 A | | 9/1921 | Bosky |
| 2,298,361 A | | 10/1942 | Freund |
| 3,173,420 A | * | 3/1965 | Mazzoni et al. ............... 450/38 |
| 3,518,998 A | | 7/1970 | Barg |
| 3,698,399 A | | 10/1972 | Hand |
| 3,968,803 A | * | 7/1976 | Hyman ......................... 450/38 |
| D258,532 S | | 3/1981 | Wagner |
| 5,098,331 A | * | 3/1992 | Corrado ........................ 450/58 |
| 5,427,563 A | * | 6/1995 | Manning .................. 450/57 X |
| 5,679,052 A | | 10/1997 | Rucki |
| 5,839,942 A | * | 11/1998 | Miller .......................... 450/58 |

* cited by examiner

Primary Examiner—Gloria M. Hale

(57) ABSTRACT

A postpartum brassiere for providing comfort to the breasts of a mother who does not breast feed. The postpartum brassiere includes a panel having an inner surface, an outer surface, a top edge, a bottom edge, a first side edge and a second side edge. A fastening member removably fastens the outer surface adjacent to the first side edge to the inner surface adjacent to the second side edge. The panel comprises a cloth material. The panel has a first section abutting the first side edge, a second section abutting the second side edge and a middle section positioned between the first and second sections. Each of a pair of pockets is attached to the inner surface of the panel and positioned on the middle section. Each of a pair of gel packs is positionable in one of the pockets.

12 Claims, 2 Drawing Sheets

POSTPARTUM BRASSIERE

BACKGROUND OF THE INVENTION

1. Field of the Invention

The present invention relates to brassieres and more particularly pertains to a new postpartum brassiere for providing comfort to the breasts of a mother who does not breast-feed.

2. Description of the Prior Art

The use of brassieres is known in the prior art. More specifically, brassieres heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,679,052; U.S. Pat. No. 2,298,361; U.S. Pat. No. 3,698,399; U.S. Pat. No. 3,518,998; U.S. Pat. No. 1,391,936; and U.S. Des. Pat. No. 258,532.

While these devices fulfill their respective, particular objectives and requirements, the aforementioned patents do not disclose a new postpartum brassiere. The inventive device includes a panel having an inner surface, an outer surface, a top edge, a bottom edge, a first side edge and a second side edge. A fastening member removably fastens the outer surface adjacent to the first side edge to the inner surface adjacent to the second side edge. The panel comprises a cloth material. The panel has a first section abutting the first side edge, a second section abutting the second side edge and a middle section positioned between the first and second sections. Each of a pair of pockets is attached to the inner surface of the panel and positioned on the middle section. Each of a pair of gel packs is positionable in one of the pockets.

In these respects, the postpartum brassiere according to the present invention substantially departs from the conventional concepts and designs of the prior art, and in so doing provides an apparatus primarily developed for the purpose of providing comfort to the breasts of a mother who does not breast feed.

SUMMARY OF THE INVENTION

In view of the foregoing disadvantages inherent in the known types of brassieres now present in the prior art, the present invention provides a new postpartum brassiere construction wherein the same can be utilized for providing comfort to the breasts of a mother who does not breast feed.

The general purpose of the present invention, which will be described subsequently in greater detail, is to provide a new postpartum brassiere apparatus and method which has many of the advantages of the brassieres mentioned heretofore and many novel features that result in a new postpartum brassiere which is not anticipated, rendered obvious, suggested, or even implied by any of the prior art brassieres, either alone or in any combination thereof.

To attain this, the present invention generally comprises a panel having an inner surface, an outer surface, a top edge, a bottom edge, a first side edge and a second side edge. A fastening member removably fastens the outer surface adjacent to the first side edge to the inner surface adjacent to the second side edge. The panel comprises a cloth material. The panel has a first section abutting the first side edge, a second section abutting the second side edge and a middle section positioned between the first and second sections. Each of a pair of pockets is attached to the inner surface of the panel and positioned on the middle section. Each of a pair of gel packs is positionable in one of the pockets.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new postpartum brassiere apparatus and method which has many of the advantages of the brassieres mentioned heretofore and many novel features that result in a new postpartum brassiere which is not anticipated, rendered obvious, suggested, or even implied by any of the prior art brassieres, either alone or in any combination thereof.

It is another object of the present invention to provide a new postpartum brassiere which may be easily and efficiently manufactured and marketed.

It is a further object of the present invention to provide a new postpartum brassiere which is of a durable and reliable construction.

An even further object of the present invention is to provide a new postpartum brassiere which is susceptible of a low cost of manufacture with regard to both materials and labor, and which accordingly is then susceptible of low prices of sale to the consuming public, thereby making such postpartum brassiere economically available to the buying public.

Still yet another object of the present invention is to provide a new postpartum brassiere which provides in the apparatuses and methods of the prior art some of the advantages thereof, while simultaneously overcoming some of the disadvantages normally associated therewith.

Still another object of the present invention is to provide a new postpartum brassiere for providing comfort to the breasts of a mother who does not breast feed.

Yet another object of the present invention is to provide a new postpartum brassiere which includes a panel having an inner surface, an outer surface, a top edge, a bottom edge, a first side edge and a second side edge. A fastening member removably fastens the outer surface adjacent to the first side edge to the inner surface adjacent to the second side edge. The panel comprises a cloth material. The panel has a first section abutting the first side edge, a second section abutting the second side edge and a middle section positioned between the first and second sections. Each of a pair of pockets is attached to the inner surface of the panel and positioned on the middle section. Each of a pair of gel packs is positionable in one of the pockets.

Still yet another object of the present invention is to provide a new postpartum brassiere that provides cooling relief and pressure to the breasts of a wearer.

Even still another object of the present invention is to provide a new postpartum brassiere that FOCUSED2.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
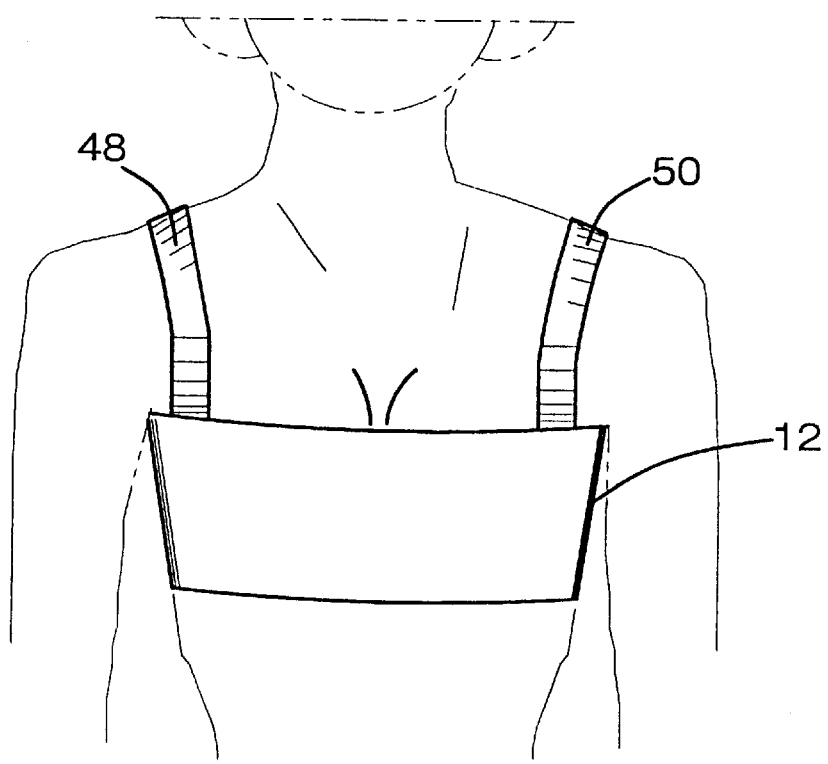
FIG. 1 is a schematic front view of a new postpartum brassiere according to the present invention.
Figure 2:
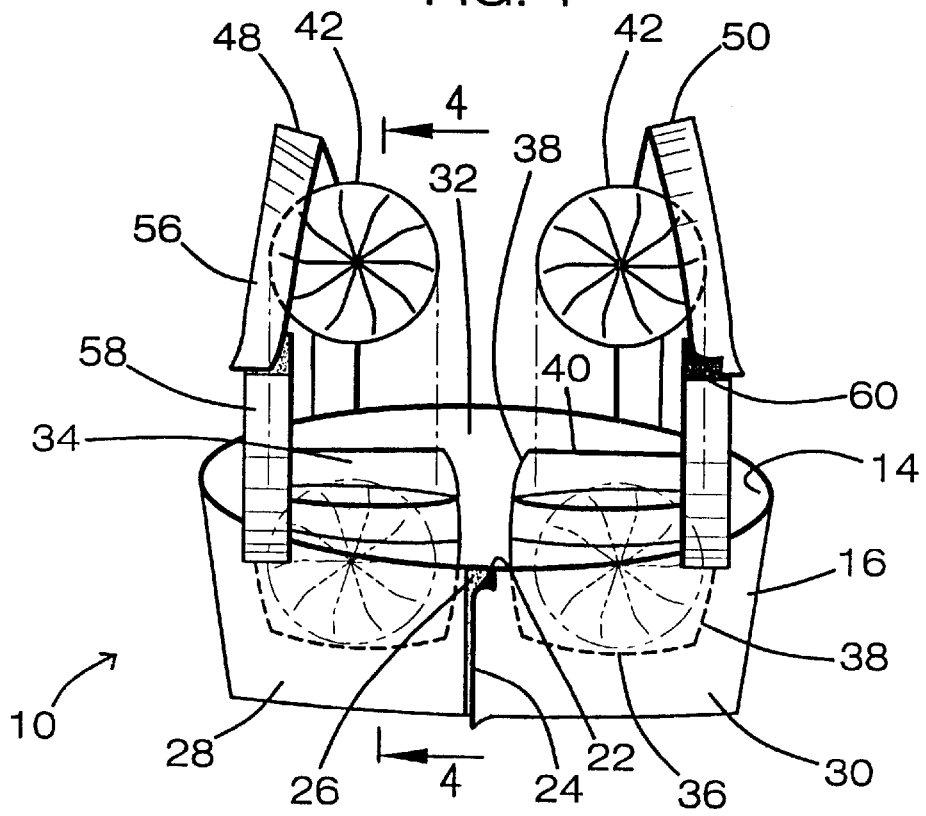
FIG. 2 is a schematic back view of the present invention.
Figure 3:
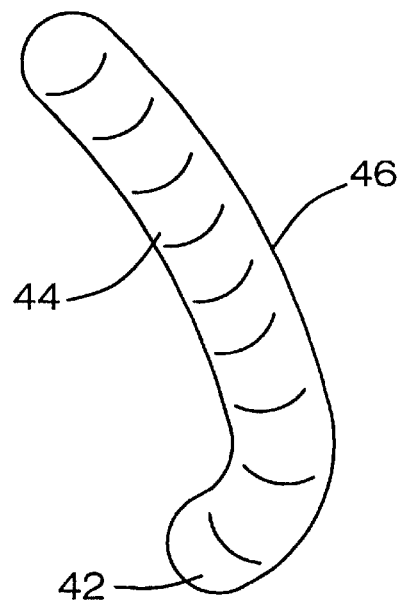
FIG. 3 is a schematic side view of the gel pack of the present invention.
Figure 4:
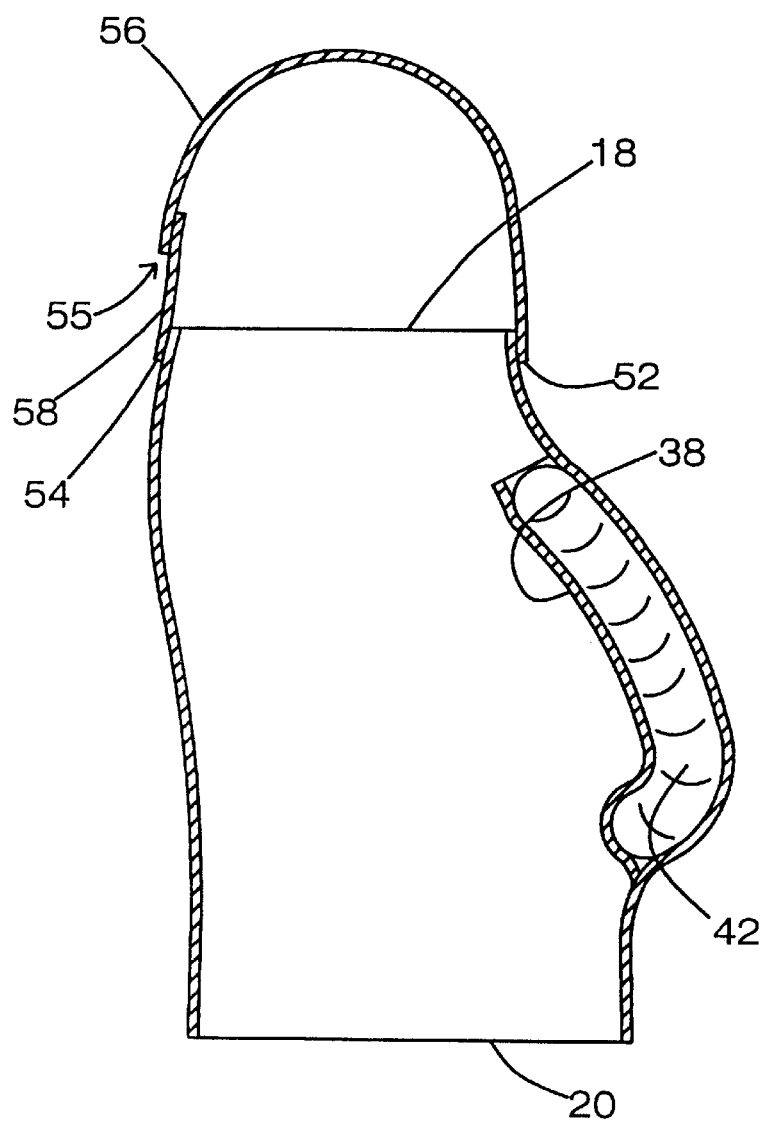
FIG. 4 is a schematic cross-sectional view taken along line 4—4 in FIG. 2 of the present invention.

With reference now to the drawings, and in particular to FIGS. 1 through 4 thereof, a new postpartum brassiere embodying the principles and concepts of the present invention and generally designated by the reference numeral 10 will be described.

As best illustrated in FIGS. 1 through 4, the postpartum brassiere 10 generally comprises a panel 12 having an inner surface 14, an outer surface 16, a top edge 18, a bottom edge 20, a first side edge 22 and a second side edge 24. A fastening member 26 removably fastens the outer surface 16 adjacent to the first side edge 22 to the inner surface 14 adjacent to the second side edge 24. The fastening member 26 comprises a hook and loop securing means. The panel 12 comprises a resiliently stretchable cloth material such as a spandex material. The panel 12 has a length generally between 35 inches and 45 inches and a height extending between the top 18 and bottom 20 edges generally between 4 inches and 8 inches, though these measurements may be altered for different wearers of the device. The panel 12 has a first section 28 abutting the first side edge 22, a second section 30 abutting the second side edge 24 and a middle section 32 positioned between the first 28 and second 30 sections. The middle section 32 defines a front portion of the panel.

Each of a pair of pockets 34 is attached to the inner surface 14 of the panel 12 and positioned on the middle section 32. Each of the pockets 34 is positioned generally adjacent to one of the first 28 and second 30 sections of the panel 12. Each of the pockets 34 comprises a cloth sheet having a generally rectangular shape. The sheets have a bottom edge 36 and a pair of side edges 38 secured to the panel 12 such that an opening, is defined between a top edge 40 of the sheets and the panel 12.

Each of a pair of gel packs 42 has a generally circular shape and has a gel material located therein. Ideally, the gel packs 42 have a concave first side 44 and a convex second side 46. The gel packs 42 are conventional gel packs 42 which may be refrigerated. Each of the gel packs is positionable in one of the pockets 38.

Each of a pair of straps 48, 50 has a first end 52 and a second end 54. The first end 52 of a first strap 48 is securely attached to the outer surface 16 of the middle section 32 of the panel 12 and positioned generally adjacent to the first section 28. The second end 54 of the first strap 48 is securely attached to the first section 28 of the panel. The first end 52 of a second strap 50 is securely attached to the outer surface 16 of the middle section 32 of the panel and positioned generally adjacent to the second section 30. The second end 54 of the second strap 50 is securely attached to the second section 30 of the panel 12. Each of the first 52 and second 54 ends of the straps 48, 50 is located generally adjacent to the top edge 18 of the panel 12. Each of the straps 48, 50 has a break 55 therein such that a first 56 and second 58 portion of each of the straps is defined. The breaks 55 are located nearer the second ends 54 than the first ends 52. Each of a pair of securing members 60 removably secures one of the first portions 56 to a respective second portion 58. Each of the securing members 60 comprises a hook and loop securing means.

In use, the gel packs 42 are cooled to a temperature below 55 degrees Fahrenheit before being placed in the pockets 38. Each of the straps 48, 50 is placed around one of the arms of a user as shown in FIG. 1. The inner surface 14 of the middle portion 32 is abutted against a chest of a user such that each of the pockets 38 is abuts one of the breasts of the user. The panel 12 is secured about the chest cavity of the user. The pressure of the panel 12 and the cooling nature of the gel packs 42 provides comfort to the wearer from pain associated with the cessation of lactation.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A postpartum brassiere comprising:
   a panel having an inner surface, an outer surface, a top edge, a bottom edge, a first side edge and a second side edge, a fastening member for removably fastening said outer surface adjacent to said first side edge to said inner surface adjacent to said second side edge, said panel comprising a cloth material, said panel having a first section abutting said first side edge, a second section abutting said second side edge and a middle section positioned between said first and second sections;
   a pair of pockets, each of said pockets being attached to said inner surface of said panel and positioned on said middle section; and
   a pair of gel packs, each of said gel packs being positionable in one of said pockets, each of said gel packs having a first side and a second side, each of said first sides being arcuate and concave, each of said second sides being arcuate and convex, wherein said gel packs are positioned in said pockets such that said second sides abut said middle section of said panel.

2. The postpartum brassiere as in claim 1, wherein said panel has a length generally between 35 inches and 45 inches.

3. The postpartum brassiere as in claim 1, wherein said panel has a height extending between said top and bottom edges generally between 4 inches and 8 inches.

4. The postpartum brassiere as in claim 1, wherein each of said pockets is positioned generally adjacent to one of said first and second sections of said panel.

5. The postpartum brassiere as in claim 4, wherein each of said pockets comprises a cloth sheet having a generally rectangular shape, each of said sheets having a bottom edge and a pair of side edges secured to said panel such that an opening is defined between a top edge of said sheets and said panel.

6. The postpartum brassiere as in claim 1, wherein each of said gel packs has a generally circular shape and having a gel material located therein.

7. The postpartum brassiere as in claim 1, further including:
   a pair of straps each having a first end and a second end, said first end of a first strap being securely attached to said outer surface of said middle section of said panel and positioned generally adjacent to said first section, said second end of said first strap being securely attached to said first section of said panel, said first end of a second strap being securely attached to said outer surface of said middle section of said panel and positioned generally adjacent to said second section, said second end of said second strap being securely attached to said second section of said panel, each of said first and second ends of said straps being located generally adjacent to said top edge of said panel.

8. The postpartum brassiere as in claim 7, wherein each of said straps has a break therein such that a first and second portion of each of said straps is defined, said breaks being located nearer said second ends than said first ends, each of a pair of securing members removably securing one of said first portions to a respective second portion.

9. A postpartum brassiere comprising:
   a panel having an inner surface, an outer surface, a top edge, a bottom edge, a first side edge and a second side edge, a fastening member for removably fastening said outer surface adjacent to said first side edge to said inner surface adjacent to said second side edge, said fastening member comprising a hook and loop securing means, said panel comprising a resiliently stretchable cloth material, said panel having a length generally between 35 inches and 45 inches, said panel having a height extending between said top and bottom edges generally between 4 inches and 8 inches, said panel having a first section abutting said first side edge, a second section abutting said second side edge and a middle section positioned between said first and second sections, said middle section defining a front portion of said panel;
   a pair of pockets, each of said pockets being attached to said inner surface of said panel and positioned on said middle section, each of said pockets being positioned generally adjacent to one of said first and second sections of said panel, each of said pockets comprising a cloth sheet having a generally rectangular shape, each of said sheets having a bottom edge and a pair of side edges secured to said panel such that an opening is defined between a top edge of said sheets and said panel;
   a pair of gel packs, each of said gel packs having a generally circular shape and having a gel material located therein, each of said gel packs being positionable in one of said pockets; and
   a pair of straps each having a first end and a second end, said first end of a first strap being securely attached to said outer surface of said middle section of said panel and positioned generally adjacent to said first section, said second end of said first strap being securely attached to said first section of said panel, said first end of a second strap being securely attached to said outer surface of said middle section of said panel and positioned generally adjacent to said second section, said second end of said second strap being securely attached to said second section of said panel, each of said first and second ends of said straps being located generally adjacent to said top edge of said panel, each of said straps having a break therein such that a first and second portion of each of said straps is defined, said breaks being located nearer said second ends than said first ends, each of a pair of securing members removably securing one of said first portions to a respective second portion, each of said securing members comprising a hook and loop securing means.

10. A method of wearing a postpartum brassiere comprising the steps of:
   providing a panel having an inner surface, an outer surface, a top edge, a bottom edge, a first side edge and a second side edge, a fastening member for removably fastening said outer surface adjacent to said first side edge to said inner surface adjacent to said second side edge, said fastening member comprising a hook and loop securing means, said panel comprising a resiliently stretchable cloth material, said panel being having a first section abutting said first side edge, a second section abutting said second side edge and a middle section positioned between said first and second sections, said middle section defining a front portion of said panel;
   providing a pair of pockets, each of said pockets being attached to said inner surface of said panel and positioned on said middle section;

providing a pair of gel packs;

providing a pair of straps each having a first end and a second end, said first end of a first strap being securely attached to said outer surface of said middle section of said panel and positioned generally adjacent to said first section, said second end of said first strap being securely attached to said first section of said panel, said first end of a second strap being securely attached to said outer surface of said middle section of said panel and positioned generally adjacent to said second section, said second end of said second strap being securely attached to said second section of said panel, each of said first and second ends of said straps being located generally adjacent to said top edge of said panel;

cooling the gel packs to a temperature below 55 degrees Fahrenheit;

positioning each of said gel packs in one of said pockets;

placing each of the straps around one of the arms of a user;

abutting said inner surface of said middle portion against a chest of a user such that each of said pockets is abutting a breast of said user; and securing said panel about the chest cavity of the user.

11. A postpartum brassiere comprising:

a panel having an inner surface, an outer surface, a top edge, a bottom edge, a first side edge and a second side edge, a fastening member for removably fastening said outer surface adjacent to said first side edge to said inner surface adjacent to said second side edge, said panel comprising a cloth material, said panel having a first section abutting said first side edge, a second section abutting said second side edge and a middle section positioned between said first and second sections;

a pair of pockets, each of said pockets being attached to said inner surface of said panel and positioned on said middle section;

a pair of straps each having a first end and a second end, said first end of a first strap being securely attached to said outer surface of said middle section of said panel and positioned generally adjacent to said first section, said second end of said first strap being securely attached to said first section of said panel, said first end of a second strap being securely attached to said outer surface of said middle section of said panel and positioned generally adjacent to said second section, said second end of said second strap being securely attached to said second section of said panel, each of said first and second ends of said straps being located generally adjacent to said top edge of said panel, each of said straps having a break therein such that a first and second portion of each of said straps is defined, said breaks being located nearer said second ends than said first ends, each of a pair of securing members removably securing one of said first portions to a respective second portion, said securing members comprising a hook and loop securing means; and a pair of gel packs, each of said gel packs being positionable in one of said pockets.

12. The postpartum brassiere as in claim 11, wherein each of said gel packs has a first side and a second side, each of said first sides being arcuate and concave, each of said second sides being arcuate and convex, wherein said gel packs are positioned in said pockets such that said second sides abut said middle section of said panel.

* * * * *